United States Patent [19]

Dugar et al.

[11] Patent Number: 5,698,548
[45] Date of Patent: Dec. 16, 1997

[54] SPIROCYCLOALKYL-SUBSTITUTED AZETIDINONES USEFUL AS HYPOCHOLESTEROLEMIC AGENTS

[75] Inventors: Sundeep Dugar, Bridgewater; John W. Clader, Cranford; Duane A. Burnett, Fanwood, all of N.J.

[73] Assignee: Schering Corporation, Kenilworth, N.J.

[21] Appl. No.: 449,980

[22] Filed: May 25, 1995

Related U.S. Application Data

[63] Continuation-in-part of PCT/US94/00421, Jan. 19, 1994, which is a continuation-in-part of Ser. No. 6,439, Jan. 21, 1993, abandoned.

[51] Int. Cl.$^6$ ............... A61K 31/395; C07D 205/12; C07P 7/10
[52] U.S. Cl. ............................ 514/210; 540/203
[58] Field of Search ............................ 540/203

[56] References Cited

U.S. PATENT DOCUMENTS

| | | | |
|---|---|---|---|
| 4,692,515 | 9/1987 | Georgiev et al. | 540/203 |
| 4,983,597 | 1/1991 | Yang et al. | 514/210 |
| 5,130,425 | 7/1992 | Malamas | 540/203 |

FOREIGN PATENT DOCUMENTS

| | | |
|---|---|---|
| 337549 | 10/1989 | European Pat. Off. |
| 1356145 | 6/1974 | United Kingdom. |
| 93/02048 | 2/1993 | WIPO. |

OTHER PUBLICATIONS

*Indian J. Chem, Sect. B*, 293, 12 (1990), pp. 1134–1137.
Schnitzer–Polokoff, et al, *Comp. Biochem. Physiol.*, 99A, 4 (1991), pp. 665–670.
Le Blanc, et al, *Tetrahedron Let.*, 33, 15 (1992), pp. 1993–1996.
*Chemical Abstracts*, 90, 11 (1979), abstract No. 87242k.
*Chemical Abstracts*, 97, 9 (1982), abstract No. 72198w.
*Chemical Abstracts*, 74, 21 (1971), abstract No. 111819w.
Salisbury, et al, *Atherosclerosis*, 115 (1995), pp. 45–63.
Harwood et al, *J. Lipid Research*, 34 (1993), pp. 377–395.
Bergman et al, XII International Symposium on Drugs Affecting Metabolism, Nov. 7–10, 1995.
Illingworth, *Drugs*, 36 (Supp. 3) (1988), pp. 63–71.
Witzum, *Circulation*, 80, 5 (1989), pp. 1101–1114.

*Primary Examiner*—Mark L. Berch
*Attorney, Agent, or Firm*—Anita W. Magatti

[57] ABSTRACT

Novel compounds of the formula

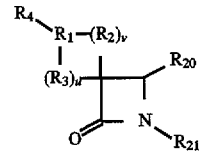

or a pharmaceutically acceptable salt thereof, wherein:
$R_1$ is

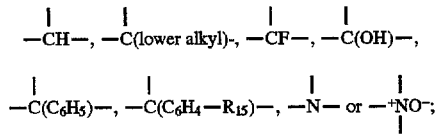

$R_2$ and $R_3$ are independently selected from —$CH_2$—, —CH(lower alkyl)—, —C(di-lower alkyl)—, —CH=CH— and —C(lower alkyl)=CH—; or $R_1$ with $R_2$, or $R_1$ with $R_3$, form —CH=CH— or —CH=C(lower alkyl)—;
u and v are independently 0–3, provided both are not zero;
$R_4$ is B—$(CH_2)_m$C(O)—; m is 0–5;
  B—$(CH_2)_q$—; q is 0–6;
  B—$(CH_2)_e$—Z—$(CH_2)_r$; Z is —O—, —C(O)—, phenylene, —N($R_8$)— or —S(O)$_{0-2}$—, e and r is 0–5; the sum of e and r is 0–6;
  B—($C_2$-$C_6$ alkenylene)—; B'—($C_4$-$C_6$ alkadienylene)—;
  B—$(CH_2)_t$—Z—($C_2$-$C_6$ alkenylene)—; t is 0–3; the sum of t and the number of carbon atoms in the alkenylene chain is 2–6;
  B—$(CH_2)_f$—V—$(CH_2)_g$—; V is cycloalkylene, f is 1–5, g is 0–5; the sum of f and g is 1–6;
  B—$(CH_2)_t$—V—($C_2$-$C_6$ alkenylene)— or B'—($C_2$-$C_6$ alkenylene)—V—$(CH_2)_t$—; the sum of t and the number of carbon atoms in the alkenylene chain is 2–6,
  B—$(CH_2)_a$—Z—$(CH_2)_b$—V—$(CH_2)_d$—; a, b and d are 0–6; the sum of a, b and d is 0–6;
  T—$(CH_2)_s$—; T is cycloalkyl, s is 0–6; or
  $R_1$ and $R_4$ together form

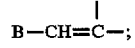

B is optionally-substituted phenyl, indanyl, indenyl, naphthyl, tetrahydronaphthyl or optionally substituted-heteroaryl; and $R_{20}$ and $R_{21}$ are independently optionally-substituted phenyl, optionally-substituted naphthyl, indanyl, indenyl, tetrahydronaphthyl, benzodioxolyl, optionally-substituted heteroaryl, optionally-substituted benzofused heteroaryl or cyclopropyl, pharmaceutical compositions, the use as hypocholesterolemic agents, processes for preparing, and the use in combination with cholesterol biosynthesis inhibitors to treat or prevent athersclerosis.

12 Claims, No Drawings

SPIROCYCLOALKYL-SUBSTITUTED AZETIDINONES USEFUL AS HYPOCHOLESTEROLEMIC AGENTS

CROSS REFERENCE TO RELATED APPLICATIONS

This application is a continuation-in-part of International Application No. PCT/US94/00421, filed Jan. 19, 1994, which is a continuation-in-part of U.S. patent application Ser. No. 08/006,439, filed Jan. 21, 1993, now abandoned.

BACKGROUND OF THE INVENTION

The present invention relates to spirocycloalkyl-substituted azetidinones useful as hypocholesterolemic agents in the treatment and prevention of atherosclerosis, and to the combination of a spirocycloalkyl-substituted azetidinone of this invention and a cholesterol biosynthesis inhibitor for the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male sex, cigarette smoke and serum cholesterol. A total cholesterol level in excess of 225–250 mg/dl is associated with significant elevation of risk.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of dietary cholesterol.

A few azetidinones have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in *Indian J Chem., Sect. B.* 29B, 12 (1990), p. 1134–7, disclose ethyl 4-(2-oxoazetidin-4-yl)phenoxy-alkanoates as hypolipidemic agents.

European Patent Application 337,549 discloses elastase inhibitory substituted azetidinones comprising a spirocyclo substituent at the 3-position; elastase inhibitors are said to be useful in treating inflammatory conditions resulting in tissue destruction which are associated with various disease states, e.g. atherosclerosis.

PCT/US92/05972, filed Jul. 21, 1992, and published as WO93/02048 on Feb. 4, 1993 discloses β-lactam (i.e., azetidinone) cholesterol absorption inhibitors which lack a spirocycloalkyl group at the 3-position.

In addition to regulation of dietary cholesterol, the regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

The inhibition of cholesterol biosynthesis by 3-hydroxy-3-methylglutaryl coenzyme A reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY Of THE INVENTION

Novel hypocholesterolemic compounds of the present invention are represented by the formula I

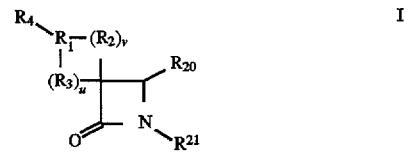

or a pharmaceutically acceptable salt thereof, wherein:
$R_1$ is

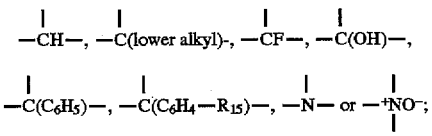

$R_2$ and $R_3$ are independently selected from the group consisting of —$CH_2$—, —CH(lower alkyl)—, —C(dilower alkyl)—, —CH=CH— and —C(lower alkyl)=CH—; or $R_1$ together with an adjacent $R_2$, or $R_1$ together with an adjacent $R_3$, form a —C=CH— or a —C=C(lower alkyl)— group;

u and v are independently 0, 1, 2 or 3, provided both are not zero; provided that when $R_2$ is —CH=CH— or —C(lower alkyl)=CH—, v is 1; provided that when $R_3$ is —CH=CH— or —C(lower alkyl)=CH—, u is 1; provided that when v is 2 or 3, the $R_2$'s can be the same or different; and provided that when u is 2 or 3, the $R_3$'s can be the same or different;

$R_4$ is B—$(CH_2)_mC(O)$—, wherein m is 0, 1, 2, 3, 4 or 5; B—$(CH_2)_q$—, wherein q is 0, 1, 2, 3, 4, 5 or 6; B—$(CH_2)_e$—Z—$(CH_2)_r$—, wherein Z is —O—, —C(O)—, phenylene, —$N(R_8)$— or —$S(O)_{0-2}$—, e is 0, 1, 2, 3, 4 or 5 and r is 0, 1, 2, 3, 4 or 5, provided that the sum of e and r is 0, 1, 2, 3, 4, 5 or 6; B—($C_2$-$C_6$ alkenylene)—; B'—($C_4$-$C_6$ alkadienylene)—; B—$(CH_2)_t$—Z—($C_2$-$C_6$ alkenylene)—, wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or 6;

B—(CH$_2$)$_t$—V—(C$_2$-C$_6$ alkenylene)— or B'—(C$_2$-C$_6$ alkenylene)—V—(CH$_2$)$_t$—, wherein V and t are as defined above, provided that the sum of t and the number of carbon atoms in the alkenylene chain is 2, 3, 4, 5 or 6;

B—(CH$_2$)$_a$—Z—(CH$_2$)$_b$—V—(CH$_2$)$_d$—, wherein Z and V are as defined above and a, b and d are independently 0, 1, 2, 3, 4, 5 or 6, provided that the sum of a, b and d is 0, 1, 2, 3, 4, 5 or 6;

T—(CH$_2$)$_s$—, wherein T is cycloalkyl of 3–6 carbon atoms and s is 0, 1, 2, 3, 4, 5 or 6; or R$_1$ and R$_4$ together form the group

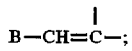

B is indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

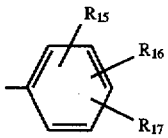

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —CF$_3$, —OCF$_3$, benzyl, R$_7$-benzyl, benzyloxy, R$_7$-benzyloxy, phenoxy, R$_7$-phenoxy, dioxolanyl, NO$_2$, —N(R$_8$)(R$_9$), N(R$_8$)(R$_9$)-lower alkylene—, N(R$_8$)(R$_9$)-lower alkylenyloxy—, OH, halogeno, —CN, —N$_3$, —NHC(O)OR$_{10}$, —NHC(O)R$_{10}$, R$_{11}$O$_2$SNH—, (R$_{11}$O$_2$S)$_2$N—, —S(O)$_2$NH$_2$, —S(O)$_{0-2}$R$_8$, tert-butyldimethylsilyloxymethyl, —C(O)R$_{12}$, —COOR$_{19}$, —CON(R$_8$)(R$_9$), —CH=CHC(O)R$_{12}$, —lower alkylene—C(O)R$_{12}$, R$_{10}$C(O)(lower alkylenyloxy)—, N(R$_8$)(R$_9$)C(O)(lower alkylenyloxy)— and

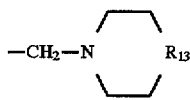

for substitution on ring carbon atoms, and the substituents on the substituted heteroaryl ring nitrogen atoms, when present, are selected from the group consisting of lower alkyl, lower alkoxy, —C(O)OR$_{10}$, —C(O)R$_{10}$, OH, N(R$_8$)(R$_9$)-lower alkylene—, N(R$_8$)(R$_9$)-lower alkylenyloxy—, —S(O)$_2$NH$_2$ and 2-(trimethylsilyl)ethoxymethyl;

R$_7$ is 1–3 groups independently selected from the group consisting of lower alkyl, lower alkoxy, —COOH, NO$_2$, —N(R$_8$)(R$_9$), OH or halogeno;

R$_8$ and R$_9$ are independently H or lower alkyl;

R$_{10}$ is lower alkyl, phenyl, R$_7$-phenyl, benzyl or R$_7$-benzyl;

R$_{11}$ is OH, lower alkyl, phenyl, R$_7$-phenyl or R$_7$-benzyl;

R$_{12}$ is H, OH, alkoxy, phenoxy, benzyloxy,

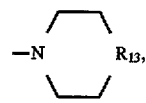

—N(R$_8$)(R$_9$), lower alkyl, phenyl or R$_7$-phenyl;

R$_{13}$ is —O—, —CH$_2$—, —NH—, —N(lower alkyl)— or —NC(O)R$_{19}$;

R$_{15}$, R$_{16}$ and R$_{17}$ are independently selected from the group consisting of H and the groups defined for W; or R$_{15}$ is hydrogen and R$_{16}$ and R$_{17}$, together with adjacent carbon atoms to which they are attached, form a dioxolanyl ring;

R$_{19}$ is H, lower alkyl, phenyl or phenyl lower alkyl; and

R$_{20}$ and R$_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

One group of preferred compounds of formula I is that wherein R$_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl, wherein W is lower alkyl, lower alkoxy, OH, halogeno, —N(R$_8$)(R$_9$), —NHC(O)OR$_{10}$, —NHC(O)R$_{10}$, NO$_2$, —CN, —N$_3$, —SH, —S(O)$_{0-2}$—(lower alkyl), —COOR$_{19}$, —CON(R$_8$)(R$_9$), —COR$_{12}$, phenoxy, benzyloxy, —OCF$_3$, —CH=C(O)R$_{12}$ or tert-butyldimethylsilyloxy, wherein R$_8$, R$_9$, R$_{10}$, R$_{12}$ and R$_{19}$ are as defined for formula I. When W is 2 or 3 substituents, the substituents can be the same or different.

Another group of preferred compounds of formula I is that wherein R$_{20}$ is phenyl or W-substituted phenyl, wherein preferred meanings of W are as defined above for preferred definitions of R$_{21}$.

More preferred are compounds of formula I wherein R$_{20}$ is phenyl or W-substituted phenyl and R$_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl; W is lower alkyl, lower alkoxy, OH, halogeno, —N(R$_8$)(R$_9$), —NHC(O)OR$_{10}$, —NHC(O)R$_{10}$, NO$_2$, —CN, —N$_3$, —SH, —S(O)$_{0-2}$—(lower alkyl), —COOR$_{19}$, —CON(R$_8$)(R$_9$), —COR$_{12}$, phenoxy, benzyloxy, —CH=CHC(O)R$_{12}$, —OCF$_3$ or tert-butyl-dimethylsilyloxy, wherein when W is 2 or 3 substituents, the substituents can be the same or different, and wherein R$_8$, R$_9$, R$_{10}$, R$_{12}$ and R$_{19}$ are as defined in formula I.

Also preferred are compounds of formula I wherein R$_1$ is

or

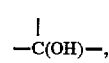

Another group of preferred compounds of formula I is that wherein R$_2$ and R$_3$ are each —CH$_2$— and the sum of u and v is 2, 3 or 4, with u=v=2 being more preferred. R$_4$ is preferably B—(CH$_2$)$_q$— or B—(CH$_2$)$_e$— Z—(CH$_2$)$_r$—, wherein B, Z, q, e and r are as defined above. B is preferably

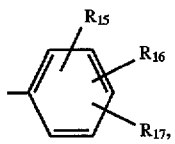

wherein $R_{16}$ and $R_{17}$ are each hydrogen and wherein $R_{15}$ is preferably H, OH, lower alkoxy, especially methoxy, or halogeno, especially chloro. A preferred definition of Z is —O—, e is preferably 0, and r is preferably 0. A preferred definition of q is 0–2. $R_{20}$ is preferably phenyl or W-substituted phenyl. Preferred W substituents for $R_{20}$ are lower alkoxy, especially methoxy and ethoxy, OH, and —C(O)$R_{12}$, wherein $R_{12}$ is preferably lower alkoxy. Preferred definitions for $R_{21}$ are phenyl, lower alkoxy-substituted phenyl and F-phenyl.

Especially preferred are compounds of formula I wherein $R_1$ is

or

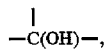

$R_2$ and $R_3$ are each —CH$_2$—, u=v=2, $R_4$ is B—(CH$_2$)$_q$—, wherein B is phenyl or phenyl substituted by lower alkoxy or chloro, q is 0–2, $R_{20}$ is phenyl, OH-phenyl, lower alkoxy-substituted phenyl or lower alkoxycarbonyl-substituted phenyl, and $R_{21}$ is phenyl, lower alkoxy-substituted phenyl or F-phenyl.

This invention also relates to a method of lowering the serum cholesterol level in a mammal in need of such treatment comprising administering an effective amount of a compound of formula I. That is, the use of a compound of the present invention as an hypocholesterolemic agent is also claimed.

In still another aspect, the present invention relates to a pharmaceutical composition comprising a serum cholesterol-lowering effective amount of a compound of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a spirocycloalkyl-substituted azetidinone cholesterol absorption inhibitor of this invention and a cholesterol biosynthesis inhibitor. That is, the present invention relates to the use of a spirocycloalkyl-substituted azetidinone cholesterol absorption inhibitor for combined use with a cholesterol biosynthesis inhibitor (and, similarly, use of a cholesterol biosynthesis inhibitor for combined use with a spirocycloalkyl-substituted azetidinone cholesterol absorption inhibitor) to treat or prevent atherosclerosis or to reduce plasma cholesterol levels In yet another aspect, the invention relates to a pharmaceutical composition comprising an effective amount of a spirocycloalkyl-substituted azetidinone cholesterol absorption inhibitor, a cholesterol biosynthesis inhibitor, and a pharmaceutically acceptable carrier. In a final aspect, the invention relates to a kit comprising in one container an effective amount of a spirocycloalkyl-substituted azetidinone cholesterol absorption inhibitor in a pharmaceutically acceptable carrier, and in a separate container, an effective amount of a cholesterol biosynthesis inhibitor in a pharmaceutically acceptable carrier.

DETAILED DESCRIPTION

As used herein, the term "lower alkyl" means straight or branched alkyl chains of 1 to 6 carbon atoms and "lower alkyoxy" similarly refers to alkoxy groups having 1 to 6 carbon atoms.

"Alkenyl" means straight or branched carbon chains having one or more double bonds in the chain, conjugated or unconjugated, and alkadienyl refers to chains having two double bonds in the chain.

Where an alkyl or alkenyl chain joins two other variables and is therefore bivalent, the terms alkylene and alkenylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Heteroaryl" includes all positional isomers for a given heteroaryl group as defined above, for example 2-pyridyl, 3-pyridyl and 4-pyridyl. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl.

"Phenylene" means a bivalent phenyl group, including ortho, meta and para-substitution.

"(Lower alkoxyimino)lower alkyl" refers to the group $(C_1-C_6$ lower alkoxy)—N=CH—$(C_1-C_5$ lower alkyl). "Lower alkanedioyl" means radicals of the formula —OC(O)(CH$_2$)$_{1-4}$C(O)OH, while "lower alkyl lower alkanedioyl" means radicals of the formula —OC(O)(CH$_2$)$_{1-4}$C(O)O-(lower alkyl).

$R_7$-benzyl and $R_7$-benzyloxy refer to benzyl and benzyloxy radicals which are substituted on the phenyl ring.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting enantiomeric starting materials or by separating isomers of a compound of formula I. Isomers may also include geometric isomers, e.g. when a double bond is present. All such geometric isomers are contemplated for this invention.

For compounds of the invention wherein $R_1$ is not N, at least two diastereomeric forms are possible. The following formulae IA and IB represent structures designated herein as "diastereomer A", wherein the lactam carbonyl group and the $R_4$ group are SYN, and "diastereomer B", wherein the lactam carbonyl group and the $R_4$ group are ANTI, respectively:

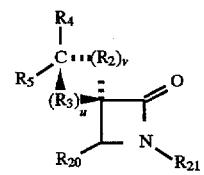

IA

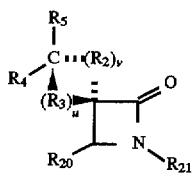

IB wherein $R_5$ is hydrogen, lower alkyl, fluoro, hydroxy, phenyl, or $R_{15}$-substituted phenyl, and $R_2$, $R_3$, $R_4$, $R_{15}$, $R_{20}$, $R_{21}$, u and v are as defined above.

Those skilled in the art will appreciate that for some compounds of formula I, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin and Cl-981; HMG CoA synthetase inhibitors, for example L-659,699 ((E,E-11-[3'R-(hydroxymethyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride). Preferred HMG CoA reductase inhibitors are lovastatin, pravastatin and simvastatin.

Compounds of formula I, wherein $R_1$, $R_2$, $R_3$, $R_4$, $R_{20}$, $R_{21}$, u and v are as defined above, can be prepared by known methods as shown in the following processes A to F.

Process A

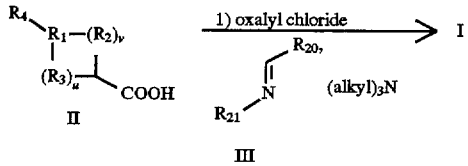

A carboxylic acid of formula II can be converted to the corresponding acid chloride by refluxing with a reagent such as oxalyl chlorine in an inert solvent such as $CH_2Cl_2$. The acid chloride is then refluxed with an imine of formula III in an inert solvent such as $CH_2Cl_2$, heptane or toluene, in the presence of a trialkylamine (i.e., $(alkyl)_3N$) such as triethylamine, tributylamine or diisopropylethylamine. Generally, all possible diastereomers of formula I are produced by this process.

Process B

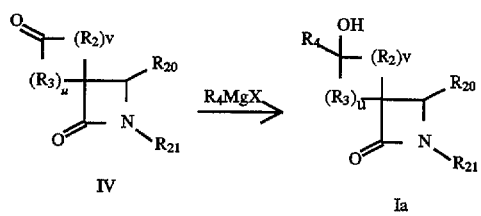

A keto-azetidinone of formula IV can be converted to a carbinol of formula Ia, i.e., a compound of formula I wherein $R_1$ is

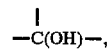
—C(OH)—, by treatment with a Grignard reagent of formula $R_4MgX$, wherein $R_4$ is as defined above and X is a halogen such as bromine, chlorine or iodine.

Process C

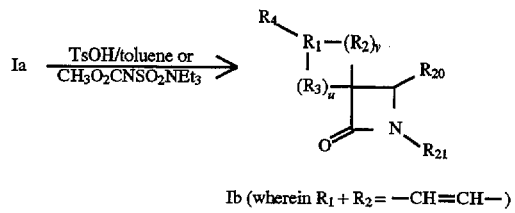

Ib (wherein $R_1 + R_2 = $ —CH=CH—)

A carbinol of formula Ia is converted to an olefin of formula Ib, wherein $R_1$ and an adjacent $R_2$ form a double bond (other $R_2$ groups can also be present) by dehydration with a mild acid such as p-toluenesulfonic acid (p-TsOH) under anhydrous conditions, e.g., using toluene as a solvent, or by treatment with a dehydrating agent such as (methoxycarbonylsulfamoyl)-triethylammonium hydroxide inner salt.

Process D

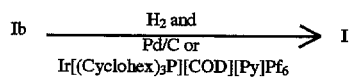

An olefin of formula Ib is reduced with hydrogen in the presence of a suitable catalyst such as palladium or an iridinium salt to obtain the desired azetidinone of formula I. When the iridinium salt is used, the resulting products have primarily the ANTI stereochemistry, IB.

Keto-azetidinone starting materials of formula IV can be prepared, for example, by the following processes:

Process E

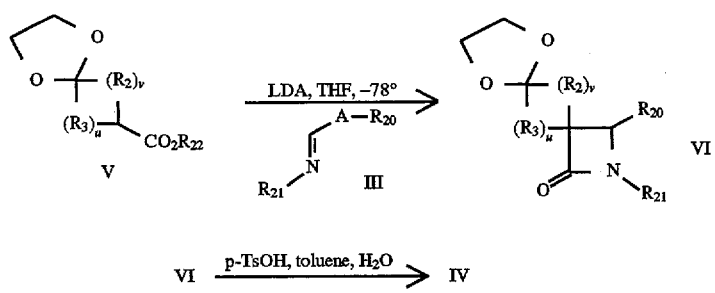

VI $\xrightarrow{\text{p-TsOH, toluene, H}_2\text{O}}$ IV

A carboxylic acid ester of formula V, wherein $R_{22}$ is lower alkyl, such as ethyl, or a chiral moiety such as menthyl or 10-(diisopropylsulfonamido)-isobornyl, is treated with a strong base such as lithium diisopropylamide (LDA) in a suitable solvent such as tetrahydrofuran (THF) at $-78°$ C. An imine of formula III is added and the reaction mixture is stirred at $-78°$ C. for a suitable period, e.g., one hour, then allowed to warm to room temperature. The product of formula VI is isolated using conventional purification techniques. When the ester group $R_{22}$ is chiral, the product is non-racemic. The ketal protecting group is removed by treatment with a mild acid such as p-TsOH to obtain the keto-azetidinone of formula IV.

Process F

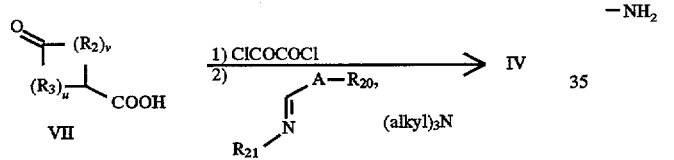

A ketoacid of formula VII can be treated with ClCOCOCl and reacted with an imine of formula III as described in Process A to obtain a keto-azetidinone of formula IV.

The carboxylic acids and imines of formulas II, III, V and VII used as starting materials in the above process are known in the art or can be prepared by one skilled in the art using well known procedures. Typical procedures for preparing a variety of carboxylic acids are described below in Preparations 1 to 6.

Reactive groups not involved in the above processes can be protected during the reactions with conventional protecting groups which can be removed by standard procedures after the reaction. The following Table 3 shows some typical protecting groups:

TABLE 3

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH$_2$OCH$_2$CH$_2$Si(CH$_3$)$_3$/, \NC(O)OC(CH$_3$)$_3$/, \N-benzyl/, \NSi(CH$_3$)$_3$/, \NSi—C(CH$_3$)$_3$/ with CH$_3$ groups |
| —NH$_2$ | —N(succinimide) |
| —OH | —OCH$_3$, —OSi(CH$_3$)$_3$, —OSi—C(CH$_3$)$_3$ with CH$_3$ groups, —OC(O)alkyl |

We have found that the compounds of this invention lower serum lipid levels, in particular serum cholesterol levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the esterification and/or intestinal absorption of cholesterol; they are, therefore, useful in the treatment and prevention of atherosclerosis in mammals, in particular in humans.

The in vivo activity of the compounds of formula I can be determined by the following procedure:

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by 1M injection of ketamine and sacrificed by decapitation. Blood is collected into vacutainer tubes containing EDTA for plasma lipid analysis and the liver excised for tissue lipid analysis. Data is reported as percent reduction of lipid versus control.

The present invention also relates to a pharmaceutical composition comprising a compound of formula I and a pharmaceutically acceptable carrier. The compounds of formula I can be administered in any conventional dosage form, preferably an oral dosage form such as a capsule, tablet, powder, cachet, suspension or solution. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. P The daily hypocholesteremic dose of a compound of formula I is about 7 to about 30 mg/kg of body weight per day. For an average body weight of 70 kg, the dosage level is therefore from about 500 to about 2000 mg of drug per day, given in a single dose or 2–4 divided doses. The exact dose, however, is determined by the attending clinician and is dependent on the potency of the compound administered, the age, weight, condition and response of the patient.

Following are examples of preparing carboxylic acid starting materials and novel compounds of formula I. The stereochemistry listed is relative stereochemistry unless otherwise noted.

Preparation 1

4-Phenyl-cyclohexanecarboxylic Acid

STEP 1: Cool a mixture of 4-phenyl-cyclohexanone (30 g) and tosylmethyl isocyanide (36.9 g) in dimethoxyethane (800 mL) in an ice/acetone bath. Add a solution of potassium t-butoxide (38.7 g) in dimethoxyethane (300 mL) and t-butanol (300 mL). Stir the reaction mixture for 4 h, pour into water and extract the product with ethyl acetate (EtOAc). Separate the organic layer, concentrate and use in STEP 2 without purification.

STEP 2: Dissolve the product from STEP 1 (32.8 g) in $CH_3OH$ (240 mL) and add water (800 mL), $Ba(OH)_2$ (95 g) and NaOH (7.8 g). Heat the reaction mixture at reflux for 24 h. Remove most of the $CH_3OH$ under vacuum and extract the aqueous solution with ether ($Et_2O$). Separate the aqueous layer, acidify with conc. HCl and extract the product with $Et_2O$. Concentrate the ether solution to obtain the title compound (17.6 g).

4-Phenyl-4-methyl-cyclohexanecarboxylic acid is similarly prepared from 4-phenyl-4-methyl-cyclohexanone.

Preparation 2

4-(4-Chlorophenyl)-cyclohexanecarboxylic Acid

STEP 1: Slowly add 4-chlorophenylmagnesium chloride (5.9 mL of 1M solution) to a solution of ethyl 4-oxo-cyclohexanecarboxylate (1.0 g) in $Et_2O$ at 0° C. After 1 h, pour the reaction mixture into 1N HCl and extract with $Et_2O$. Separate the organic layer, wash with water, brine and concentrate to give ethyl 4-(4-chlorophenyl)-4-hydroxy-cyclohexanecarboxylate (1.75 g) which is used without purification in the next step.

STEP 2: Dissolve the product (1.75 g) from STEP 1 in THF (100 mL), treat with 40% $H_2SO_4$ (25 mL) and heat the reaction mixture at reflux for 5.5 h. Remove most of the solvent in vacuo, dilute the reaction mixture with water and extract with $Et_2O$. Separate the organic layer and concentrate to give 4-(4-chlorophenyl)-cyclohex-3-enecarboxylic acid (1.36 g).

STEP 3: Reduce a solution of the product of STEP 2 (1.36 g) in EtOAc (50 mL) over 10% Pd/C under $H_2$ (50 psi) for 14 h. Filter the catalyst and concentrate the solution to give the title compound (1.36 g).

4-(4-Methoxyphenyl)-cyclohexanecarboxylic acid is similarly prepared.

Preparation 3

4-Cyclohexyl-cyclohexanecarboxylic Acid

Reduce a solution of 4-biphenylcarboxylic acid (10 g) in ethanol (EtOH) (175 mL) and EtOAc (30 mL) over 5% rhodium/alumina (7 g) under $H_2$ (60 psi) for 8 days. Filter the catalyst and concentrate the solution to obtain the title compound (9.92 g).

Preparation 4

4-Benzyl-cyclohexanecarboxylic Acid

STEP 1: Reduce a solution of terphthalic acid mono-methyl ester (12.6 g) using a procedure similar to that of Preparation 3 to obtain 1,4-cyclohexanedicarboxylic acid mono-methy ester (12.64 g). The crude product is used without purification in the next step.

STEP 2: Add ClCOCOCl (4.1 g) to a solution of the product of STEP 1 (3.0 g) in $CH_2Cl_2$ (15 mL) and heat the mixture at reflux for 1.5 h. Remove excess ClCOCOCl in vacuo and dissolve the product in benzene. Cool the reaction mixture in an ice/water bath and slowly add $AlCl_3$ (4.74 g). Stir the reaction mixture overnight as it warms to ambient temperature and pour into a conc. HCl/ice mixture. Extract the product with $Et_2O$, separate the organic layer, wash with water and brine, then concentrate to obtain methyl 4-(4-benzoyl)-cyclohexane-carboxylate (3.9 g).

STEP 3: Reduce a solution of the product of STEP 2 (2.5 g) in EtOAc (15 mL) and acetic acid (HOAc) (50 mL) over 10% Pd/C (0.3 g) under $H_2$ (60 psi) for 22 h. Filter the catalyst, dilute the reaction mixture with water and extract the product with $Et_2O$. Separate the organic layer and concentrate to obtain a mixture of methyl 4-($\alpha$-hydroxybenzyl)-cyclohexanecarboxylate and methyl (4-benzylcyclohexane-carboxylate (2.46 g).

STEP 4: Dissolve the product from STEP 3 (2.46 g) in THF (100 mL), treat with 40% $H_2SO_4$ (25 mL) and heat the reaction mixture at reflux for 5 h. Pour the reaction mixture into excess water and extract with EtOAc. Separate the organic layer, concentrate, and reduce the crude mixture over 10% Pd/C (0.25 g) under $H_2$ (60 psi) overnight. Filter the catalyst and concentrate the solution to obtain the title compound (2.42 g).

Preparation 5

4-(2-Phenylethyl)-cyclohexanecarboxylic Acid

STEP 1: Slowly add 2-phenylethyl bromide (2.6 g) to a slurry of Mg (0.37 g) in THF (50 mL) and heat at reflux for 4 h. Cool the solution to ambient temperature and add to a solution of ethyl 4-oxo-cyclo-hexanecarboxylate (2.4 g) in THF (50 mL). After 2 h, pour the reaction mixture into a half-saturated solution of NH₄Cl and extract with EtOAc. Partially purify the product on a silica gel column, eluting with EtOAc. Dissolve the product in toluene (100 mL), treat with p-TsOH and heat at reflux overnight with azeotropic removal of water. Cool the reaction mixture, wash with saturated NaHCO₃ solution and concentrate. Purify the crude product on a silica gel column, eluting with CH₂Cl₂ to obtain ethyl 4-(2-phenylethyl)-cyclohex-3-enecarboxylate (0.45 g) and 1-(2-phenyl-ethyl)-2-oxabicyclo[2.2.2]octan-3-one (0.71 g). Dissolve 1-(2-phenyl-ethyl)-2-oxabicyclo[2.2.2]octan-3-one in EtOH, treat with conc.HCl (catalytic) and heat at reflux overnight. Dilute the reaction mixture with water and extract with EtOAc. Concentrate the organic layer to obtain additional ethyl 4-(2-phenylethyl)-cyclohex-3-enecarboxylate (0.88 g).

STEP 2: To a solution of the product of STEP 1 (1.33 g) in EtOAc (40 mL), add 10% Pd/C (0.2 g) and hydrogenate overnight at 58 psi. Filter the catalyst and concentrate the reaction mixture to give ethyl 4-(2-phenylethyl)-cyclohexanecarboxylate (1.26 g).

STEP 3: To a solution of the product of STEP 2 (1.26 g) in MeOH (20 mL), add water (5 mL) and LiOH (0.61 g) and stir overnight at ambient temperature. Dilute the reaction mixture with water and extract with Et₂O. Acidify the aqueous layer with conc.HCl and extract with EtOAc. Separate the organic layer, wash with water and brine, and concentrate to obtain the title compound (1.06 g).

Preparation 6

3-Benzyl-cyclobutanecarboxylic Acid

STEP 1: Slowly add a solution of diethyl 2-benzylmalonate (20 g) in Et₂O (300 mL) to a slurry of LiAlH₄ (6 g) in Et₂O (300 mL), then heat the reaction mixture at reflux for 14 h. Carefully add 4N NaOH to the reaction mixture until there is no precipitate, then extract with EtOAc. Concentrate the organic layer and purify the crude product on a silica gel column, eluting with EtOAc to obtain 2-benzyl-1,3-propanediol (8.45 g).

STEP 2: Slowly add (C₆H₅)₃P (17.4 g) to a solution of the product of STEP 1 (5 g) in CH₂Cl₂ (200 mL) containing CBr₄ (21 g) at 0° C. Stir the reaction mixture overnight and allow to warm to ambient temperature. Evaporate the solvent in vacuo, triturate the crude product with pentane, filter, concentrate the filtrate and purify the residue on a silica gel column, eluting with hexane to give 2-benzyl-1,3-propanedibromide (5.47 g).

STEP 3: Add diethyl malonate (3 g) to a slurry of NAH (0.514 g) in dimethylformamide (DMF) (75 mL) at ambient temperature. After 1 h, heat the reaction mixture to 100° C. for 1 h, cool to ambient temperature, add a solution of the product of STEP 2 (5 g) in DMF (25 mL) and stir at ambient temperature for 2.5 h, followed by 2 h at 150° C. Cool the mixture to ambient temperature, add NaH (0.514 g) and after 30 min., heat at 150° C. overnight. Cool the reaction mixture, pour into excess water and extract with EtOAc. Separate the organic layer, wash with water and concentrate. Purify the crude product on a silica gel column, eluting with EtOAc:hexane (1:9) to obtain diethyl (3-benzyl)-cyclobutyl-1,1-dicarboxylate (3 g).

STEP 4: To a solution of the product of STEP 3 (3 g) in EtOH (20 mL), add water (5 mL) and KOH (2.9 g) and heat at reflux overnight. Dilute the reaction mixture with water and extract with Et₂O. Acidify the aqueous layer with conc.HCl and extract with CH₂Cl₂. Separate the organic layer and concentrat to give 3-benzyl-cyclobutyl-1,1-dicarboxylic acid (2.31 g).

STEP 5: Heat the product of STEP 4 (2.31 g) at 170°–180° C. under vacuum (60–70 mm) for 1.5 h to obtain the title compound (1.85 g).

In a similar manner, 2-(2-phenylethyl)malonate is converted to 2-(2-phenylethyl)cyclobutanecarboxylic acid.

Preparation 7

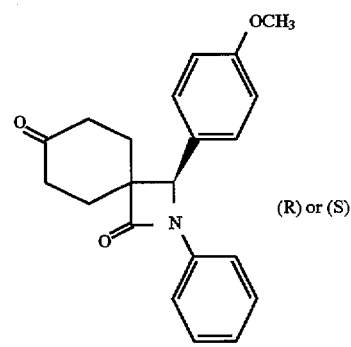

(R) or (S)

STEP 1: Heat a mixture of 4-carbomethoxycyclohexanone (4.4 g, 0.028 moles), HOCH₂CH₂OH (3.2 mL, 0.056 moles), and a catalytic amount of p-TsOH in toluene at reflux for 4 hr with continuous removal of water. Cool to room temperature, wash the organic layer with water, dry over MgSO₄, and evaporate to give the crude ketal. Dissolve ketal in MeOH (80 mL) containing KOH (5.6 g) and stir at room temperature overnight. Concentrate to dryness and dissolve in Et₂O (100 mL). Adjust to pH 2 with 1N HCl. Extract with Et₂O (3×100 mL), dry over MgSO₄ and evaporate to obtain 4.0 grams of the ethylene ketal of 4-cyclohexanonecarboxylic acid.

STEP 2: Add the product from Step 1 (0.344 g, 1.8 mmol) and 10-diisopropylsulfonamido)-isoborneol (0.570 g, 1.8 mmol) to a mixture of DCC (0.556 g, 2.7 mmol), dimethylaminopyridine (DMAP) (0.330 g, 2.7 mmol), and DMAP HCl (0.003 g) in CH₂Cl₂ (5 mL). Stir at room temp. overnight, dilute with Et₂O (150 mL) and filter. Concentrate the filtrate under vacuum and purify the crude ester by chromatography on silica gel, eluting with 30% EtOAc/hexane to obtain 0.508 grams of the ester.

STEP 3: Prepare a solution of LDA (from [(CH₃)₂CH]₂NH (0.23 mL) and 1.6M CH₃(CH₂)₃Li (1.03 mL) in hexane) in THF (5 mL), cool to −78° C. and add a solution of the product of Step 2 in THF (5 mL). Stir at −78° C. for 1.5 hr, then add a solution of (N-(4-methoxy-benzylidine) aniline (0.278 g, 1.32 mmol) in THF (5 mL). Stir this mixture at −78° C. for 1 hr and at room temperature for 1 hr. Quench the reaction with a solution of 10% aqueous KHSO₄ (20 mL), extract with EtOAc (3×20 mL), dry the organic layers over MgSO₄ and evaporate. Purify the crude product by chromatography over silica gel, eluting with 40% EtOAc/hexane to obtain 0.266 g of product.

STEP 4: Stir the product of Step 3 overnight in 5:1 acetone: 3N HCl to obtain 0.21 grams of the title compound.

If 10-diisolpropylsulfonamido)-isoborneol derived from (+)-10-camphorsulfonyl chloride is used in Step 1, the product has the (S)-configuration.

Preparation 8

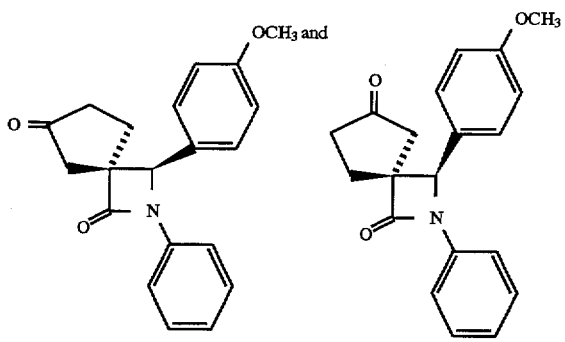

STEP 1: To a solution of ethyl 3-oxocyclopentanecarboxylate (2.63 g, 0.0169 moles) in benzene (50 mL), add HOCH$_2$CH$_2$OH (2.10 g, 0.0338 moles) and pyridinium tosylate (0.85 g, 0.0034 moles). Heat at reflux with removal of water for 2.5 hr. Remove the solvent under vacuum and take up the residue in Et$_2$O (100 mL). Wash with saturated Na$_2$CO$_3$ and concentrate to a yellow oil. Purify by chromatography on silica gel, eluting with 10% EtOAc/hexane to obtain 2.92 grams of the ketal ester.

STEP 2: React the product of Step 1 (0.30 g, 0.0015 moles) with LDA (1.2 equivalents) in THF followed by N-(4-methoxybenzylidine)aniline as described for Preparation 7, Step 3, to obtain 0.52 grams of the resulting azetidinone as a mixture of diastereomers. Separate these diastereomers by chromatography on silica gel, eluting with 20% EtOAc/hexane to obtain 0.16 grams of component A and 0.22 grams of component B.

STEP 3: Treat component A of Step 2 (1.38 g) with aqueous HCl as described for Preparation 7, Step 4, to obtain 1.15 grams of rel (3R,4R)-3-(4-methoxyphenyl)-2-phenyl-2-azaspiro[3.4]octane-1,6-dione. Similar treatment of component B yields rel (3R,4S)-3-(4-methoxyphenyl)-2-phenyl-2-azaspiro[3.4]octane-1,6-dione.

Preparation 9

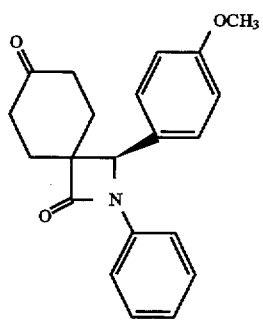

Treat a solution of 4-cyclohexanonecarboxylic acid (4.6 g, 0.0323 moles) in CH$_2$Cl$_2$ (50 mL) with ClCOCOCl (5.7 mL, 0.0648 moles) as described in Example 1, below. React the resulting acid chloride with N-(4-methoxybenzylidene) aniline using the procedure described in Example 1 to obtain the title compound (10.03 g).

In a similar manner, using N-(4-methoxybenzylidine)-4-(t-butyl-dimethylsilyloxy)aniline, prepare:

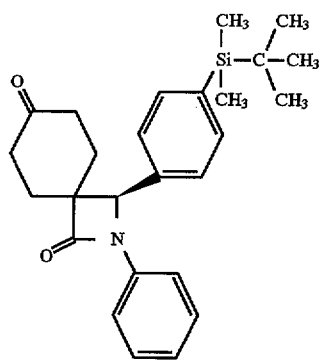

Examples 1 and 1A 2,3-Bis-(4-methoxyphenyl)-7-(4-chlorophenyl)-2-azaspiro[3.5]nonan-1-one Add ClCOCOCl (1.43 g) to a solution of the product of Preparation 2 (1.34 g) in CH$_2$Cl$_2$ (15 mL) and heat at reflux for 2 h. Remove the solvent and excess ClCOCOCl under vacuum. Dissolve the resultant acid chloride in CH$_2$Cl$_2$ (5 mL), add this solution to N-(4-methoxybenzylidene) anisidine (1.35 g) and triethylamine (Et$_3$N) (1.25 g) in CH$_2$Cl$_2$ (25 mL) and heat at reflux overnight. Pour the reaction mixture into 1N HCl and extract the product with CH$_2$Cl$_2$. Separate the organic layer, wash with saturated NaHCO$_3$ and concentrate. Purify the crude material on a silica gel column, eluting with CH$_2$Cl$_2$:hexane (95:5) to give:

(1) Diastereomer A of the title compound: 0.52 g; m.p. 166–167; Mass spectrum: Calculated 461 and observed 462; Elemental analysis: Calculated: C=72.8, H=6.11, N=3.03 Found: C=72.72, H=6.11, N=3.15

(1A) Diastereomer B of the title compound: 0.475 g; m.p. 87–89 Mass spectrum: Calculated 461 and observed 462; Elemental analysis: Calculated: C=72.8, H=6.11, N=3.03 Found: C=72.79, H=6.17, N=3.12.

Other 2-azaspiro[3.5]nonan-1-ones and 2-azaspiro[3.3]-heptan-1-ones similarly prepared are shown in the following table:

| Ex. | Dia-ster. | R₁ | −(R₂)ᵥ− | −(R₃)ᵤ− | R₄ | R₂₀ | R₂₁ | mp, °C. | MS | Elem. Anal. |
|---|---|---|---|---|---|---|---|---|---|---|
| 2 | A | CH | −(CH₂)₂− | −(CH₂)₂− | Ph | 4-OCH₃-Ph | 4-CH₃-Ph | 68–71 | Calcd: 427 Obs: 427 | Calcd: C: 78.66, H: 6.84, N: 3.28 Found: C: 78.26, H: 6.77, N: 3.36 |
| 3 | B | CH | −(CH₂)₂− | −(CH₂)₂− | Ph | 4-OCH₃-Ph | 4-CH₃-Ph | 75–77 | Calcd: 427 Obs: 427 | |
| 4 | A | CH | −(CH₂)₂− | −(CH₂)₂− | Ph | 4-OCH₃-Ph | 4-CH₃-Ph | — | Calcd: 397 Obs: 398 | Calcd: C: 81.58, H: 6.85, N: 3.52 Found: C: 81.06, H: 6.76, N: 365 |
| 5 | B | CH | −(CH₂)₂− | −(CH₂)₂− | Ph | 4-OCH₃-Ph | 4-CH₃-Ph | — | Calcd: 397 Obs: 398 | Calcd: C: 81.58, H: 6.85, N: 3.52 Found: C: 80.87, H: 6.75, N: 3.68 |
| 6 | A | CH | −(CH₂)₂− | −(CH₂)₂− | Ph | 4-OCH₂CH₃-Ph | 4-CH₃-Ph | — | Calcd: 411 Obs: 412 | Calcd: C: 81.72, H: 7.10, N: 3.40 Found: C: 81.59, H: 7.05, N: 3.60 |
| 7 | B | CH | −(CH₂)₂− | −(CH₂)₂− | Ph | 4-OCH₂CH₃-Ph | 4-CH₃-Ph | — | Calcd: 411 Obs: 411 | |
| 8 | — | N | −(CH₂)₂− | −(CH₂)₂− | Ph | 4-OCH₃-Ph | 4-OCH₃-Ph | — | Calcd: 428 Obs: 429 | Calcd: C: 75.68, H: 6.59, N: 6.54 Found: C: 75.40, H: 6.66, N: 6.52 |

-continued

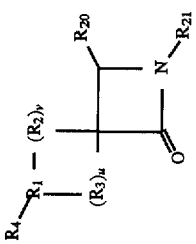

| Ex. | Dia-ster. | $R_1$ | $-(R_2)_v-$ | $-(R_3)_u-$ | $R_4$ | $R_{20}$ | $R_{21}$ | mp, °C | MS | Elem. Anal. |
|---|---|---|---|---|---|---|---|---|---|---|
| 9 | A | CH | $-(CH_2)_2-$ | $-(CH_2)_2-$ | phenyl | phenyl | 4-OCH₃-phenyl | 191–193 | Calcd: 396 Obs: 397 | Calcd: C: 81.58, H: 6.85, N: 3.52 Found: C: 81.57, H: 6.84, N: 3.55 |
| 10 | B | CH | $-(CH_2)_2-$ | $-(CH_2)_2-$ | phenyl | phenyl | 4-OCH₃-phenyl | 178–180 | Calcd: 396 Obs: 397 | Calcd: C: 81.58, H: 6.85, N: 3.52 Found: C: 81.56, H: 6.82, N: 3.56 |
| 11 | A | C(CH₃) | $-(CH_2)_2-$ | $-(CH_2)_2-$ | phenyl | 4-OCH₃-phenyl | phenyl | — | Calcd: 411 Obs: 412 | |
| 12 | B | C(CH₃) | $-(CH_2)_2-$ | $-(CH_2)_2-$ | phenyl | 4-OCH₃-phenyl | phenyl | — | Calcd: 411 Obs: 412 | |
| 13 | A | CH | $-(CH_2)_2-$ | $-(CH_2)_2-$ | phenyl | 4-COOCH₃-phenyl | 4-OCH₃-phenyl | 184–185 | Calcd: 455 Obs: 455 | Calcd: C: 76.46, H: 6.42, N: 3.07 Found: C: 76.20, H: 6.38, N: 3.07 |
| 14 | B | CH | $-(CH_2)_2-$ | $-(CH_2)_2-$ | phenyl | 4-COOCH₃-phenyl | 4-OCH₃-phenyl | 125–127 | Calcd: 455 Obs: 455 | Calcd: C: 76.46, H: 6.42, N: 3.07 Found: C: 76.36, H: 6.72, N: 3.19 |
| 15 | A | CH | $-(CH_2)_2-$ | $-(CH_2)_2-$ | 4-CH₃O-phenyl | 4-OCH₃-phenyl | phenyl | 149–150 | Calcd: 427 Obs: 428 | Calcd: C: 78.66, H: 6.84, N: 3.28 Found: C: 78.74, H: 6.89, N: 3.48 |

-continued

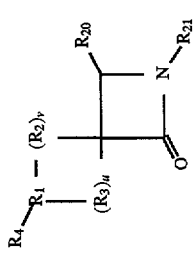

| Ex. | Dia-ster. | $R_1$ | $-(R_2)_v-$ | $-(R_3)_u-$ | $R_4$ | $R_{20}$ | $R_{21}$ | mp, °C. | MS | Elem. Anal. |
|---|---|---|---|---|---|---|---|---|---|---|
| 16 | B | CH | $-(CH_2)_2-$ | $-(CH_2)_n-$ | 4-CH$_3$O-phenyl | 4-OCH$_3$-phenyl | phenyl | 161–162 | Calcd: 427 Obs: 428 | Calcd: C: 78.66, H: 6.84, N: 3.28 Found: C: 78.53, H: 6.80; N: 3.47 |
| 17A | A | CH | $-(CH_2)_2-$ | $-(CH_2)_2-$ | phenyl | 4-SCH$_3$-phenyl | phenyl | — | Calcd: 413 Obs: 414 | — |
| 17B | B | CH | $-(CH_2)_2-$ | $-(CH_2)_2-$ | phenyl | 4-SCH$_3$-phenyl | phenyl | — | Calcd: 413 Obs: 413 | — |
| 18 | A | CH | $-(CH_2)_2-$ | $-(CH_2)_2-$ | benzyl | 4-OCH$_3$-phenyl | phenyl | 65–69 | Calcd: 411 Obs: 412 | HRMS Calcd: 412.2277 Found: 412.2272 |
| 19 | B | CH | $-(CH_2)_2-$ | $-(CH_2)_2-$ | benzyl | 4-OCH$_3$-phenyl | phenyl | 126–130 | Calcd: 411 Obs: 412 | HRMS Calcd: 412.2277 Found: 412.2269 |
| 20 | A | CH | $-(CH_2)_2-$ | $-(CH_2)_2-$ | 4-Cl-phenyl | 4-OCH$_3$-phenyl | phenyl | 167–168 | Calcd: 431 Obs: 432 | Calcd: C: 75.08, H: 6.07, N: 3.24 Found: C: 75.07, H: 6.07, N: 3.31 |
| 21 | B | CH | $-(CH_2)_2-$ | $-(CH_2)_2-$ | 4-Cl-phenyl | 4-OCH$_3$-phenyl | phenyl | 76–78 | Calcd: 431 Obs: 432 | Calcd: C: 75.08, H: 6.07, N: 3.24 Found: C: 75.28, H: 6.04, N: 3.33 |

-continued

Structure: R4—R1—(R2)v, (R3)u, with β-lactam ring bearing R20 and N-R21

| Ex. | Dia- ster. | R1 | —(R2)v— | —(R3)u— | R4 | R20 | R21 | mp, C° | MS | Elem. Anal. |
|---|---|---|---|---|---|---|---|---|---|---|
| 22* | B | CH | —(CH2)2— | —(CH2)2— | phenyl | 4-OCH3-phenyl | 4-OCH3-phenyl | 76–77 | Calcd: 427 Obs: 428 | Calcd: C: 78.85, H: 6.62, N: 3.28 Found: C: 78.84, H: 6.65, N: 3.30 |
| 23* | B | CH | —(CH2)2— | —(CH2)2— | phenyl | 4-OCH3-phenyl | 4-OCH3-phenyl | 76–77 | Calcd: 427 Obs: 428 | Calcd: C: 78.85, H: 6.62, N: 3.28 Found: C: 78.84, H: 6.65, N: 3.30 |
| 24 | A | CH | —(CH2)2— | —(CH2)2— | phenyl-(CH2)2 | 4-OCH3-phenyl | phenyl | 57–59 | Calcd: 425 Obs: 426 | Calcd: C: 81.85, H: 7.34, N: 3.29 Found: C: 81.97, H: 7.34, N: 3.21 |
| 25 | B | CH | —(CH2)2— | —(CH2)2— | phenyl-(CH2)2 | 4-OCH3-phenyl | phenyl | 53–55 | Calcd: 425 Obs: 426 | Calcd: C: 81.85, H: 7.34, N: 3.29 Found: C: 81.77, H: 7.24, N: 3.29 |
| 26* | B | CH | —(CH2)2— | —(CH2)2— | 4-Cl-phenyl | 4-OCH3-phenyl | phenyl | 174–175 | Calcd: 414 Obs: 415 | Calcd: C: 78.16, H: 6.07, N: 3.38 Found: C: 78.20, H: 6.10, N: 3.39 |
| 27* | B | CH | —(CH2)2— | —(CH2)2— | 4-Cl-phenyl | 4-OCH3-phenyl | phenyl | 174–175 | Calcd: 414 Obs: 415 | Calcd: C: 78.16, H: 6.07, N: 3.38 Found: C: 78.17, H: 6.09, N: 3.38 |
| 28 | — | —C=CH— | | —(CH2)2— | 4-Cl-phenyl | 4-OCH3-phenyl | phenyl | 163–164 | Calcd: 429 Obs: 430 | Calcd: C: 75.43, H: 5.63, N: 3.26 Found: C: 75.35, H: 5.67, N: 3.35 |

-continued

| Ex. | Dia-ster. | $R_1$ | $-(R_2)_v-$ | $-(R_3)_u-$ | $R_4$ | $R_{20}$ | $R_{21}$ | mp, C° | MS | Elem. Anal. |
|---|---|---|---|---|---|---|---|---|---|---|
| 29A | A | CH | $-CH_2-$ | $-CH_2-$ | phenyl | 4-OCH₃-phenyl | phenyl | 56–58 | Calcd: 383 Obs: 384 | Calcd: C: 81.43, H: 6.57, N: 3.65 Found: C: 81.54, H: 6.49, N: 3.56 |
| 29B | B | CH | $-CH_2-$ | $-CH_2-$ | phenyl | 4-OCH₃-phenyl | phenyl | 97–98 | Calcd: 383 Obs: 384 | Calcd: C: 81.43, H: 6.57, N: 3.65 Found: C: 81.09, H: 6.36, N: 3.42 |
| 30A | A | CH | $-CH_2-$ | $-CH_2-$ | phenyl-(CH₂)₂- | 4-OCH₃-phenyl | phenyl | | | ¹H NMR(400MHz, CDCl₃) δ6.90–7.30(m, 14H), 4.71(s, 1H), 3.82(s, 3H), 2.66(ddd, 1H, J=3.00, 7.73, 11.60), 2.29(dd, 1H, J=4.20, 7.94, 11.91), 1.94(dd, 1H, J=9.56, 11.60), 1.23(dd, 1H, J=8.54, 11.91), 2.46(m, 3H), 1.59(m, 2H) |
| 30B | B | CH | $-CH_2-$ | $-CH_2-$ | phenyl-(CH₂)₂- | 4-OCH₃-phenyl | phenyl | | | ¹H NMR(400MHz, CDCl₃) δ6.90–7.32(m, 14H), 4.87(s, 1H), 3.82(s, 3H), 2.42–2.56(m, 3H), 2.95(dd, 1H, J=7.39, 11.9), 2.05(m 1H), 1.92(dd, 1H, J=7.63, 12.2), 1.64(ddd, J=8.24, 3.36, 11.9), 1.83(q, 2H, J=7.63) |
| 31 | A | CH | $-(CH_2)_2-$ | $-(CH_2)_2-$ | cyclohexyl | 4-OCH₃-phenyl | phenyl | 180–181 | Calcd: 403 Obs: 404 | Calcd: C: 80.36, H: 8.24, N: 3.47 Found: C: 80.41, H: 8.19, N: 3.57 |

-continued

| Ex. | Dia-ster. | $R_1$ | $-(R_2)_v-$ | $-(R_3)_u-$ | $R_4$ | $R_{20}$ | $R_{21}$ | mp, °C. | MS | Elem. Anal. |
|---|---|---|---|---|---|---|---|---|---|---|
| 32 | B | CH | $-(CH_2)_2-$ | $-(CH_2)_2-$ | cyclohexyl | 4-OCH₃-phenyl | phenyl | 141–143 | Calcd: 403 Obs: 404 | Calcd: C: 80.36, H: 8.24, N: 3.47 Found: C: 80.35, H: 8.15, N: 3.74 |
| 33 | A | CH | $-(CH_2)_2-$ | $-(CH_2)_2-$ | phenyl | 4-OCH₃-phenyl | cyclopropyl | — | — | Calcd: C: 79.74, H: 7.53, N: 3.87 Found: C: 79.36, H: 7.57, N: 3.98 |
| 34 | B | CH | $-(CH_2)_2-$ | $-(CH_2)_2-$ | phenyl | 4-OCH₃-phenyl | cyclopropyl | — | Calcd: 361 Obs: 361 | — |

\* = Single Enantiomers

Enantiomeric compounds of Examples 22 and 23 were prepared by chromatographic resolution of the racemate in a CHIRACEL OD HPLC column eluting with 93:7 hexane:isopropanol at a flow rate of 5 mL/min.

Enantiomeric compounds of Examples 26 and 27 were prepared by chromatographic resolution of the racemate in a CHIRACEL OD HPLC column eluting with 95:5 hexane:isopropanol at a flow rate of 5 mL/min.

Example 26: $[\alpha]_D^{25} = +60.7°$ (CH$_3$OH)

Example 27: $[\alpha]_D^{25} = -58.1°$ (CH$_3$OH)

Examples 35A, 35B, 35C, 35D and 35E

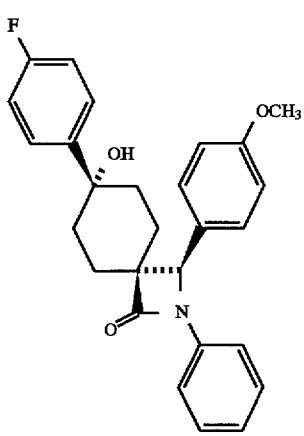

35A and

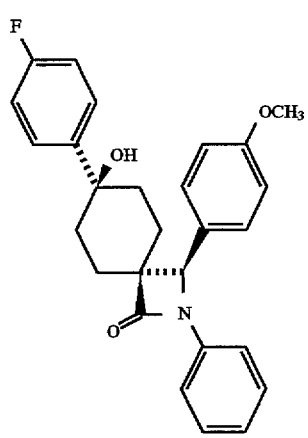

35B

To a solution of the product of Preparation 7 (1.1 g, 3.28 mmol) in Et$_2$O (20 mL) at 0° C., add a solution of 4-fluorophenylmagnesium bromide (4.9 mL, 4.92 mmol) in THF over 5 min. Stir at 0° C. for 1.5 hr, then stir at room temperature for 3 hr. Quench the reaction with sat'd NaHSO$_4$ and extract with EtOAc (3×30 mL). Dry the organic layers over Na$_2$SO$_4$ and evaporate the solvent to obtain 1.57 grams of crude product. Purify by chromatography over silica gel, eluting with 95:5 Ch$_2$Cl$_2$:EtOAc to obtain 0.9 g of the ANTI isomer, mp=168°–169° C., and 0.27 g of the SYN isomer.

In a similar manner, the following compounds are prepared:

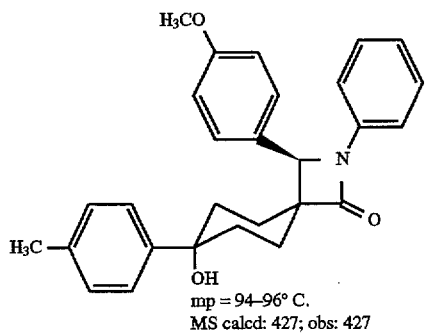

35C mp = 94–96° C.
MS calcd: 427; obs: 427

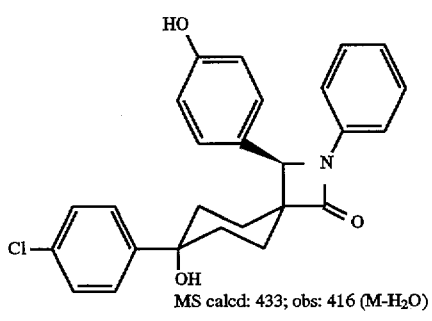

35D

MS calcd: 433; obs: 416 (M-H$_2$O)

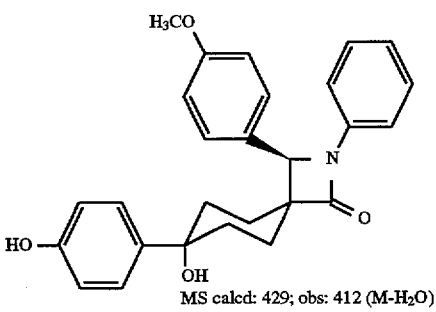

35E

MS calcd: 429; obs: 412 (M-H$_2$O)

Examples 36, 36A, 36B, 37 and 38

Using appropriate starting materials in a procedure similar to that described in Example 35, the following compounds are prepared:

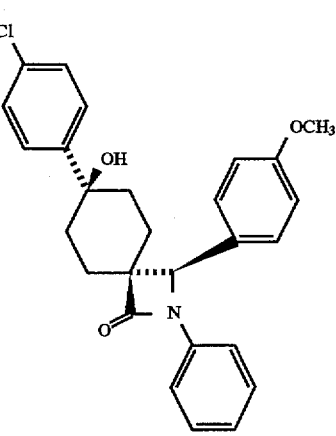

36

Examples 39, 40, 40A

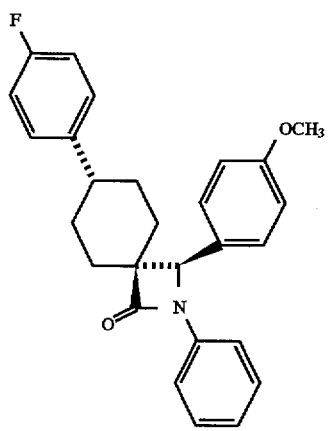

36A

36B

STEP 1: Add p-TsOH (0.08 g) to a solution of the product of Example 35 (0.5 g) and stir at 60° C. over 4A sieves for 3.5 hr. Filter the mixture through celite, wash with sat'd NaHCO$_3$, dry over Na$_2$SO$_4$, and evaporate to obtain 7-(4-fluorophenyl)-7-hydroxy-3-(4-methoxyphenyl)-2-phenyl-2-azaspiro[3.5]non-6-en-1-one, which can be used in STEP 2 with or without purification by chromatography over silica gel.

STEP 2: To a solution of the product of STEP 1, (0.415 g, 1 mmol) in CH$_2$Cl$_2$ (15 mL), add (tricyclohexylphosphine)-(1,5-cyclooactadiene)-(pyridine) Iridium(I) hexafluorophosphate (0.010 g, 0.05 mmol). Stir under one atm H$_2$ at room temperature for 52 hr. Filter the mixture through a bed of silica gel, eluting with CH$_2$Cl$_2$ to give 0.161 g of the title compound, mp=146°–147° C. MS calcd: 415; obs: 415.

In a similar manner, except using 10% Pd/C as the hydrogenation catalyst, use the compound of Example 38 as the starting material to prepare the following compounds:

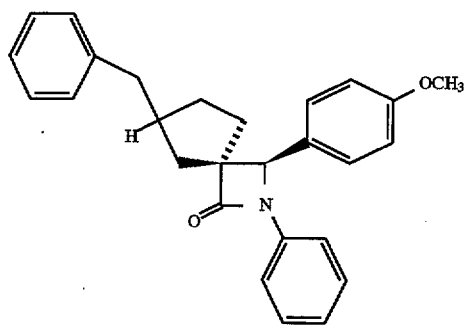

mp = 102–103° C.

40

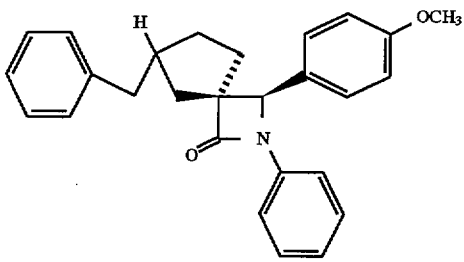

40A

CI Mass Spectrum, M/z(intensity):
398(100, M+), 279(13), 211(18).

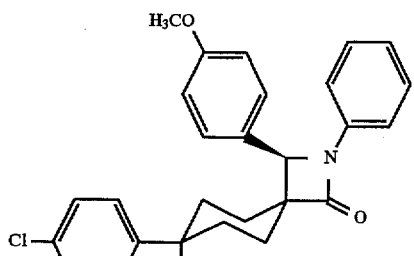

mp = 100.0–103.0° C.
[α]$_D^{20}$ = +55.9° (CH$_3$OH)
single enantiomer

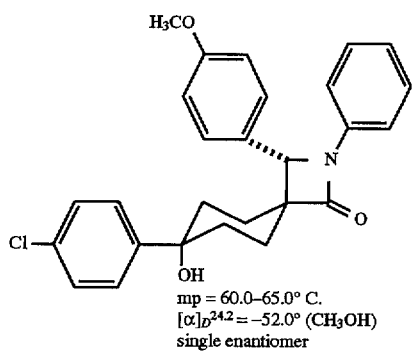

mp = 60.0–65.0° C.
[α]$_D^{24.2}$ = –52.0° (CH$_3$OH)
single enantiomer

37

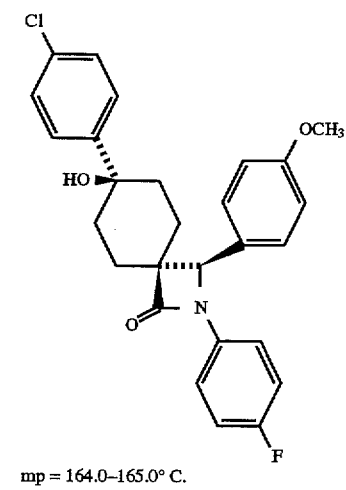

mp = 164.0–165.0° C.

38

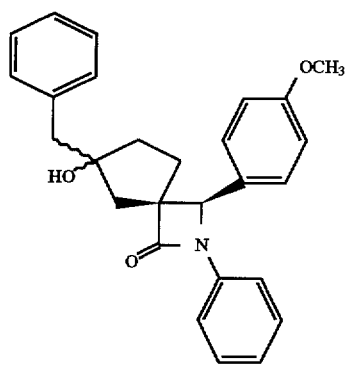

mp = 61.0–64.0° C.

Examples 41, 42 and 42A

Use the product of Preparation 8 in the procedure of Example 35, followed by the procedure of Example 39, STEP 1, to obtain the compound of Example 41. Treat the compound of Example 41 using the procedure of Example 39, STEP 2, to obtain compounds of Examples 42 and 42A:

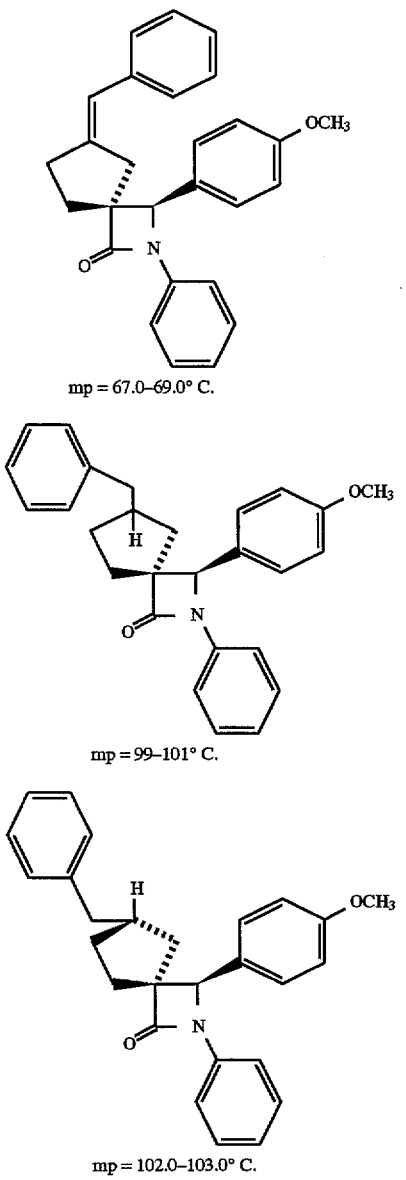

Examples 43A and 43B

Use the product of Preparation 7 in the procedure of Example 35, followed by the procedures of Example 39, STEP 1 and STEP 2, to obtain compounds of Examples 43A and 43B:

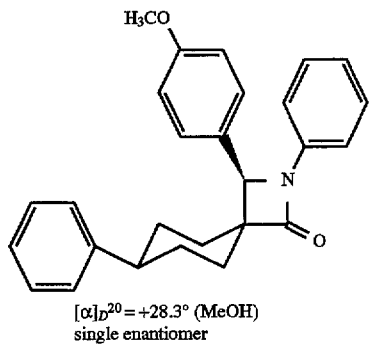

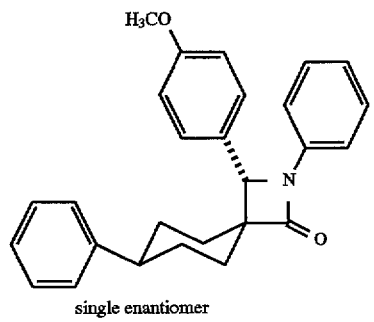

Examples 44A and 44B

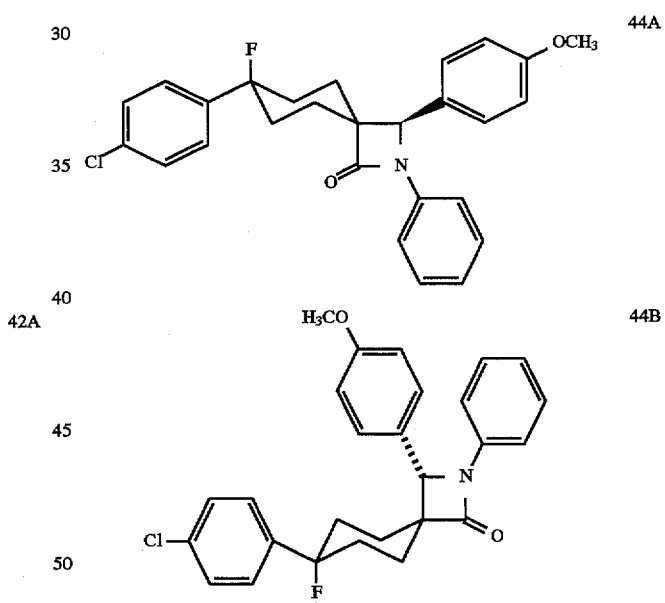

Dissolve the compound of Example 36 (0.31 g, 0.693 moles) in $CH_2Cl_2$ (7 mL) at $-78°$ C. and add dropwise, over 2–3 min., diethylamino-sulfur trifluoride (0.145 mL, 1.09 mmoles). Stir the mixture for 2 hr. at $-78°$ C. Quench the mixture with ice-cold saturated $NaHCO_3$ and extract with $CH_2Cl_2$ (2×10 mL). Dry the combined organic layers over $Na_2SO_4$ and concentrate to an oil. Purify by flash chromatography on silica gel to obtain pure SYN diastereomer (0.146 mg) and impure ANTI diastereomer (0.72 mg). Purify the ANTI diastereomer by preparative TLC on a 20×20 cm silica gel plate, eluting with $CH_2Cl_2$ to obtain 0.026 g.

The following formulations exemplify some of the dosage forms of this invention. In each the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Using the test procedures described above, the following in vivo data were obtained for the exemplified compounds. Data is reported as percent change (i.e., percent reduction in cholesterol esters) versus control, therefore, negative numbers indicate a positive lipid-lowering effect.

| Ex. No. | % Change | Dose mpk |
|---|---|---|
| 1 | −25 | 50 |
| 1A | −89 | 50 |
| 2 | −17 | 50 |
| 3 | −87 | 50 |
| 4 | 0 | 50 |
| 5 | −95 | 50 |
| 6 | −26 | 50 |
| 7 | −64 | 50 |
| 8 | −17 | 50 |
| 9 | −46 | 50 |
| 10 | 0 | 50 |
| 11 | −25 | 50 |
| 12 | −36 | 50 |
| 13 | −21 | 50 |
| 14 | −30 | 50 |
| 15 | 31 | 50 |
| 16 | 0 | 50 |
| 17A | — | — |
| 17B | — | — |
| 18 | 0 | 50 |
| 19 | −43 | 50 |
| 20 | 0 | 50 |
| 21 | −92 | 50 |
| 22 | — | |
| 23 | — | |
| 24 | 0 | 50 |
| 25 | −43 | 50 |
| 26 | −97 | 25 |
| 27 | −32 | 25 |
| 28 | −65 | 50 |
| 29A | −9 | 50 |
| 29B | 0 | 50 |
| 30A | −65 | 10 |
| 30B | −42 | 10 |
| 31 | −15 | 50 |
| 32 | −30 | 50 |
| 33 | 0 | 50 |
| 34 | 0 | 50 |
| 35A | 0 | 10 |
| 35B | −93 | 10 |
| 35C | −31 | 10 |
| 36 | −92 | 10 |
| 36A | −85 | 3 |
| | −62 | 1 |
| 36B | −18 | 3 |
| 37 | −91 | 10 |
| 38 | −21 | 10 |
| 39 | — | |
| 40 | −90 | 50 |
| | −89 | 10 |
| 40A | −65 | 10 |
| 41 | −35 | 10 |
| 42 | −84 | 50 |
| 42A | 0 | 10 |
| 43A | −75 | 10 |
| | −55.5 | 3 |
| 43B | — | |

We claim:

1. A compound represented by the formula

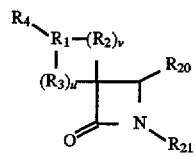

or a pharmaceutically acceptable salt thereof, wherein:

$R_1$ is

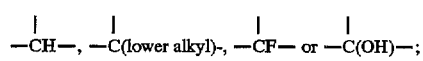

$R_2$ and $R_3$ are —$CH_2$—; or $R_1$ together with an adjacent $R_2$, or $R_1$ together with an adjacent $R_3$, form a —C=CH— group;

u and v are independently 0, 1, 2 or 3, provided both are not zero;

$R_4$ is B—$(CH_2)_q$—, wherein q is 0, 1, 2, 3, 4, 5 or 6;

T—$(CH_2)_s$—, wherein T is cycloalkyl of 3–6 carbon atoms and s is 0, 1, 2, 3, 4, 5 or 6; or $R_1$ and $R_4$ together form the group

B is thienyl, naphthyl or

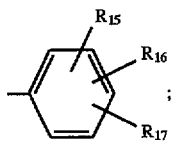

$R_8$ is H or lower alkyl;

$R_{15}$, $R_{16}$ and $R_{17}$ are independently selected from the group consisting of H and W;

W is 1 to 3 groups independently selected from the group consisting of lower alkyl, lower alkoxy, OH, halogeno, —S(O)$_{0-2}$R$_8$, —C(O)R$_{12}$, —CH=CHC(O) lower alkoxy) or —lower alkylene—C(O)R$_{12}$;

$R_{12}$ is OH or lower alkoxy; and $R_{20}$ and $R_{21}$ are independently selected from the group consisting of phenyl and W-substituted phenyl.

2. A compound of claim 1 wherein $R_1$ is

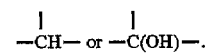

3. A compound of claim 1 wherein $R_2$ and $R_3$ are each —CH$_2$— and the sum of u and v is 2, 3 or 4.

4. A compound of claim 1 wherein $R_4$ is B—(CH$_2$)$_q$ wherein B is

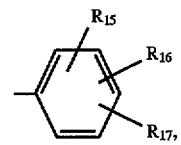

q is 0–2, $R_{16}$ is H, $R_{17}$ is H and $R_{15}$ is as defined in claim 1.

5. A compound of claim 4 wherein $R_{15}$ is H, OH, lower alkoxy or chloro.

6. A compound of claim 1 wherein $R_{20}$ is phenyl or W-substituted phenyl, wherein W is as defined in claim 1.

7. A compound of claim 6 wherein $R_{20}$ is W-substituted phenyl and W is lower alkoxy, OH or —C(O)R$_{12}$, wherein $R_{12}$ is lower alkoxy.

8. A compound of claim 1 wherein $R_{21}$ is phenyl or W-substituted phenyl, wherein W is lower alkyl, lower alkoxy, OH, halogeno, —S(O)$_{0-2}$-(lower alkyl) or —COR$_{12}$, and when W is 2 or 3 groups, the groups can be the same or different.

9. A compound of claim 1 represented by the formula

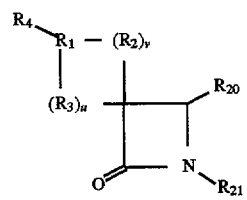

wherein $R_1$, $R_2$, $R_3$, $R_4$, $R_{20}$, $R_{21}$, u and v are as follows:

| $R_1$ | —(R$_2$)$_v$— | —(R$_3$)$_u$— | $R_4$ | $R_{20}$ | $R_{21}$ |
|---|---|---|---|---|---|
| CH | —(CH$_2$)$_2$— | —(CH$_2$)$_2$— | Cl-phenyl | phenyl-OCH$_3$ | phenyl-OCH$_3$ |
| CH | —(CH$_2$)$_2$— | —(CH$_2$)$_2$— | phenyl | phenyl-OCH$_3$ | phenyl-OCH$_3$ |
| CH | —(CH$_2$)$_2$— | —(CH$_2$)$_2$— | phenyl | phenyl-OCH$_3$ | phenyl |
| CH | —(CH$_2$)$_2$— | —(CH$_2$)$_2$— | phenyl | phenyl-OCH$_2$CH$_3$ | phenyl |
| CH | —(CH$_2$)$_2$— | —(CH$_2$)$_2$— | phenyl | phenyl | phenyl-OCH$_3$ |

-continued

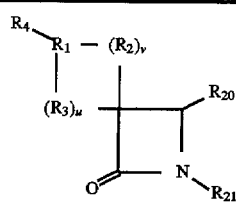

wherein $R_1$, $R_2$, $R_3$, $R_4$, $R_{20}$, $R_{21}$, u and v are as follows:

| $R_1$ | $-(R_2)_v-$ | $-(R_3)_u-$ | $R_4$ | $R_{20}$ | $R_{21}$ |
|---|---|---|---|---|---|
| $C(CH_3)$ | $-(CH_2)_2-$ | $-(CH_2)_2-$ | phenyl- | 4-$OCH_3$-phenyl- | phenyl- |
| CH | $-(CH_2)_2-$ | $-(CH_2)_2-$ | phenyl- | 4-$COOCH_3$-phenyl- | 4-$OCH_3$-phenyl- |
| CH | $-(CH_2)_2-$ | $-(CH_2)_2-$ | phenyl- | 4-$SCH_3$-phenyl- | phenyl- |
| CH | $-(CH_2)_2-$ | $-(CH_2)_2-$ | phenyl-$CH_2-$ | 4-$OCH_3$-phenyl- | phenyl- |
| CH | $-(CH_2)_2-$ | $-(CH_2)_2-$ | 4-Cl-phenyl- | 4-$OCH_3$-phenyl- | phenyl- |
| CH | $-(CH_2)_2-$ | $-(CH_2)_2-$ | phenyl-$(CH_2)_2-$ | 4-$OCH_3$-phenyl- | phenyl- |
| $-\overset{\mid}{C}=CH-$ | | $-(CH_2)_2-$ | 4-Cl-phenyl- | 4-$OCH_3$-phenyl- | phenyl- |
| CH | $-CH_2-$ | $-CH_2-$ | phenyl- | 4-$OCH_3$-phenyl- | phenyl- |
| CH | $-CH_2-$ | $-CH_2-$ | phenyl-$(CH_2)_2-$ | 4-$OCH_3$-phenyl- | phenyl- |
| CH | $-(CH_2)_2-$ | $-(CH_2)_2-$ | cyclohexyl- | 4-$OCH_3$-phenyl- | phenyl- |
| $-\overset{\mid}{C}(OH)-$ | $-(CH_2)_2-$ | $-(CH_2)_2-$ | 4-F-phenyl- | 4-$OCH_3$-phenyl- | phenyl- |
| $-\overset{\mid}{C}(OH)-$ | $-(CH_2)_2-$ | $-(CH_2)_2-$ | 4-$H_3C$-phenyl- | 4-$OCH_3$-phenyl- | phenyl- |

-continued

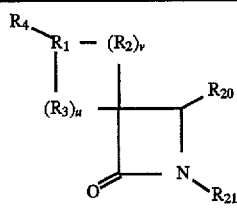

wherein $R_1$, $R_2$, $R_3$, $R_4$, $R_{20}$, $R_{21}$, u and v are as follows:

| $R_1$ | $-(R_2)_v-$ | $-(R_3)_u-$ | $R_4$ | $R_{20}$ | $R_{21}$ |
|---|---|---|---|---|---|
| $-\overset{\mid}{C}(OH)-$ | $-(CH_2)_2-$ | $-(CH_2)_2-$ | Cl-C₆H₄- | HO-C₆H₄- | C₆H₅- |
| $-\overset{\mid}{C}(OH)-$ | $-(CH_2)_2-$ | $-(CH_2)_2-$ | HO-C₆H₄- | CH₃O-C₆H₄- | C₆H₅- |
| $-\overset{\mid}{C}(OH)-$ | $-(CH_2)_2-$ | $-(CH_2)_2-$ | Cl-C₆H₄- | CH₃O-C₆H₄- | C₆H₅- |
| $-\overset{\mid}{C}(OH)-$ | $-(CH_2)_2-$ | $-(CH_2)_2-$ | Cl-C₆H₄- | CH₃O-C₆H₄- | F-C₆H₄- |
| $-\overset{\mid}{C}(OH)-$ | $-(CH_2)_2-$ | $-CH_2-$ | C₆H₅-CH₂- | CH₃O-C₆H₄- | C₆H₅- |
| CH | $-(CH_2)_2-$ | $-(CH_2)_2-$ | F-C₆H₄- | CH₃O-C₆H₄- | C₆H₅- |
| CH | $-(CH_2)_2-$ | $-CH_2-$ | C₆H₅-CH₂- | CH₃O-C₆H₄- | C₆H₅- |
| see $R_4$ | $-CH_2-$ | $-(CH_2)_2-$ | $R_1$ and $R_4$ together are C₆H₅-C=C⟨ | CH₃O-C₆H₄- | C₆H₅- |
| CH | $-CH_2-$ | $-(CH_2)_2-$ | C₆H₅-CH₂- | CH₃O-C₆H₄- | C₆H₅- |
| $-\overset{\mid}{C}(F)-$ | $-(CH_2)_2-$ | $-(CH_2)_2-$ | Cl-C₆H₄- | CH₃O-C₆H₄- | C₆H₅- |

10. A compound of claim 1 selected from the group consisting of:

7-(4-chlorophenyl)-3-(4-methoxyphenyl)-2-phenyl-2-azaspiro[3.5]nonan-1-one;

7-(4-chlorophenyl)-7-hydroxy-3-(4-methoxyphenyl)-2-phenyl-2-azaspiro[3.5]nonan-1-one;

7-(4-chlorophenyl)-2-(4-fluorophenyl)-7-hydroxy-3-(4-methoxyphenyl)-2-azaspiro[3.5]nonan-1-one; and 7-(4-chlorophenyl)-7-hydroxy-3-(4-hydroxyphenyl)-2-phenyl-2-azaspiro[3.5]nonan-1-one.

11. A pharmaceutical composition comprising an amount of a compound of claim 1 effective to lower serum cholesterol, or treat or prevent atherosclerosis, in a pharmaceutically acceptable carrier.

12. A method of lowering the serum cholesterol level, or treating or preventing atherosclerosis, in a mammal in need of such treatment comprising administering an effective amount of a compound of claim 1.

* * * * *

UNITED STATES PATENT AND TRADEMARK OFFICE
CERTIFICATE OF CORRECTION

PATENT NO. : 5,698,548
DATED : DECEMBER 16, 1997
INVENTOR(S) : SUNDEEP DUGAR ET AL

It is certified that error appears in the above-identified patent and that said Letters Patent is hereby corrected as shown below:

In column 36, sixth line from the bottom, in the definition of $R_2$ and $R_3$, change $-C=CH-$ to $-\overset{|}{C}=CH-$ .

Signed and Sealed this

Third Day of March, 1998

*Attest:*

*Attesting Officer*

BRUCE LEHMAN

*Commissioner of Patents and Trademarks*